United States Patent
Mansouri

(10) Patent No.: US 10,080,764 B2
(45) Date of Patent: *Sep. 25, 2018

(54) TOPICAL MINOCYCLINE COMPOSITIONS AND METHODS OF USING THE SAME

(71) Applicant: Laboratory Skin Care, Inc., South San Francisco, CA (US)

(72) Inventor: Zahra Mansouri, South San Francisco, CA (US)

(73) Assignee: Laboratory Skin Care, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,829

(22) Filed: Dec. 15, 2016

(65) Prior Publication Data

US 2017/0189427 A1    Jul. 6, 2017

Related U.S. Application Data

(63) Continuation of application No. 13/944,373, filed on Jul. 17, 2013, now Pat. No. 9,539,266, which is a continuation of application No. PCT/US2012/021926, filed on Jan. 19, 2012.

(60) Provisional application No. 61/434,368, filed on Jan. 19, 2011.

(51) Int. Cl.
| | |
|---|---|
| *A61K 31/65* | (2006.01) |
| *A61K 9/00* | (2006.01) |
| *A61K 33/06* | (2006.01) |
| *A61K 33/42* | (2006.01) |
| *A61K 9/14* | (2006.01) |

(52) U.S. Cl.
CPC ............ *A61K 31/65* (2013.01); *A61K 9/0014* (2013.01); *A61K 9/14* (2013.01); *A61K 33/06* (2013.01); *A61K 33/42* (2013.01); *Y10T 428/2982* (2015.01)

(58) Field of Classification Search
CPC .... A61K 2300/00; A61K 31/65; A61K 33/06; A61K 33/42; A61K 9/0014; A61K 9/14; Y10T 428/2982
See application file for complete search history.

(56) References Cited

U.S. PATENT DOCUMENTS

| | | | |
|---|---|---|---|
| 4,701,320 A | 10/1987 | Hasegawa et al. | |
| 4,869,906 A * | 9/1989 | Dingeldein | A61L 24/0015 424/423 |
| 4,948,575 A | 8/1990 | Cole et al. | |
| 5,158,756 A | 10/1992 | Ogawa et al. | |
| 5,604,200 A | 2/1997 | Taylor-McCord | |
| 5,607,980 A * | 3/1997 | McAtee | A61K 8/416 424/78.02 |
| 5,674,539 A | 10/1997 | Tomas | |
| 6,096,324 A | 8/2000 | Mansouri | |
| 6,120,782 A | 9/2000 | Mansouri | |
| 6,262,020 B1 | 7/2001 | Lezdey et al. | |
| 6,395,311 B2 | 5/2002 | Jia | |
| 6,573,249 B2 | 6/2003 | Lezdey et al. | |
| 8,445,002 B2 * | 5/2013 | Mansouri | A61K 31/355 424/400 |
| 8,535,723 B2 * | 9/2013 | Ogawa | A61K 9/0014 424/489 |
| 9,707,177 B2 * | 7/2017 | Mansouri | A61K 31/525 |
| 2002/0018797 A1 | 2/2002 | Cui et al. | |
| 2003/0018587 A1 | 1/2003 | Althoff et al. | |
| 2003/0185871 A1 * | 10/2003 | Nathan | A61L 27/18 424/426 |
| 2004/0180091 A1 | 9/2004 | Lin | |
| 2005/0013874 A1 | 1/2005 | Ito et al. | |
| 2005/0234114 A1 | 10/2005 | Lee | |
| 2006/0025735 A1 | 2/2006 | Berg et al. | |
| 2006/0257358 A1 * | 11/2006 | Wen | A61K 9/0021 424/85.1 |
| 2006/0257658 A1 | 11/2006 | Tanaka et al. | |
| 2007/0003487 A1 | 1/2007 | Ek | |
| 2007/0012824 A1 | 1/2007 | Ryser et al. | |
| 2007/0128245 A1 * | 6/2007 | Rosenberg | A61K 9/0024 424/423 |
| 2008/0051335 A1 | 2/2008 | Kleiner et al. | |
| 2008/0063681 A1 * | 3/2008 | Simon | A61K 6/0625 424/423 |
| 2008/0220233 A1 | 9/2008 | Kjellin et al. | |
| 2009/0214601 A1 | 8/2009 | Chappa et al. | |
| 2010/0086606 A1 * | 4/2010 | Ogawa | A61K 9/0014 424/489 |
| 2012/0130435 A1 | 5/2012 | Hart et al. | |
| 2012/0134919 A1 | 5/2012 | Engqvist et al. | |
| 2012/0207803 A1 | 8/2012 | Bell | |
| 2014/0199400 A1 * | 7/2014 | Ogawa | A61K 9/0014 424/490 |

FOREIGN PATENT DOCUMENTS

| | | |
|---|---|---|
| EP | 1514538 A1 | 3/2005 |
| EP | 1797900 A1 | 6/2007 |
| JP | 2008291010 A | 12/2008 |
| WO | 200015194 A1 | 3/2000 |
| WO | 2005084637 A2 | 9/2005 |
| WO | 2008041846 A2 | 4/2008 |
| WO | 2010129819 A2 | 11/2010 |

OTHER PUBLICATIONS

Kasten et al (Acta Biomaterialia, 2008, vol. 4, pp. 1904-1915).*
Meisel M., "About Face, Anti-aging, natural products lead the thriving skin care category" Happi Household and Personal Products Industry. (May 7, 2008) web article: http://www.happi.com/articles/2008/05/about-face; 15 pages.
Kasten et al., Porosity and pore size of beta-tricalcium phosphate scaffold can influence protein production and osteogenic differentiation of human mesenchymal stem cells: an in vitro and in vivo study, Acta Biomater. Nov. 2008;4(6):1904-15.

\* cited by examiner

*Primary Examiner* — Mark V Stevens
(74) *Attorney, Agent, or Firm* — Bret E. Field; Bozicevic, Field & Francis LLP

(57) ABSTRACT

Topical minocycline compositions with reduced fluorescence are provided. In some instances, the compositions include an amount of a minocycline active agent associated with porous calcium particles. Also provided are methods of using the compositions, e.g., in the treatment of acne.

20 Claims, 5 Drawing Sheets

TOPICAL MINOCYCLINE COMPOSITIONS AND METHODS OF USING THE SAME

CROSS-REFERENCE TO RELATED APPLICATIONS

Pursuant to 35 U.S.C. § 119 (e), this application claims priority to the filing date of U.S. Provisional Patent Application Ser. No. 61/434,368 filed Jan. 19, 2011; the disclosure of which application is herein incorporated by reference.

INTRODUCTION

Oral tetracycline-class antibiotics are frequently used in the treatment of acne. Tetracycline-class antibiotics are known to have some side effects. These side effects include vestibular symptoms such as vertigo, dizziness or blurred vision. These effects are sometimes disabling. See, Gould & Brookler, Arch. Otolarang. Vol. 96, p. 291 (1972); Williams et al., Lancet, Sep. 28, 1974, p. 144-45; Fanning & Gump, Arch. Intern. Med., Vol. 136, pp. 761-62 (1976). Headache and general malaise, along with gastro-intestinal symptoms such as the diarrhea, nausea, gas, or cramps may also occur. Dry nose and dry mouth are also occasionally encountered. One of the oral tetracycline-class antibiotics used in the treatment of acne is minocycline hydrochloride. Oral dosage forms of minocycline hydrochloride are available commercially under various trade names. The Approved Drug Products with Therapeutic Equivalence Evaluations ("Orange Book") lists a number of oral dosage forms of minocycline hydrochloride that are AB-rated to the MINOCIN® brand of minocycline hydrochloride. These commercial products are immediate-release oral dosage forms of minocycline hydrochloride that have been determined by the Food and Drug Administration (FDA) to be therapeutically equivalent to the MINOCIN® brand of minocycline hydrochloride on the basis of adequate in vivo and/or in vitro evidence supporting bioequivalence.

SUMMARY

Topical minocycline compositions are provided. In some instances, the compositions include an amount of minocycline associated with porous calcium particles, e.g., via entrapment in the pores of the particles and/or ionic binding and/or non-covalent binding to the surface of the particles and/or loosely associated with the particles. Also provided are methods of using the compositions, e.g., in the treatment of acne.

DETAILED DESCRIPTION

Figure 1:
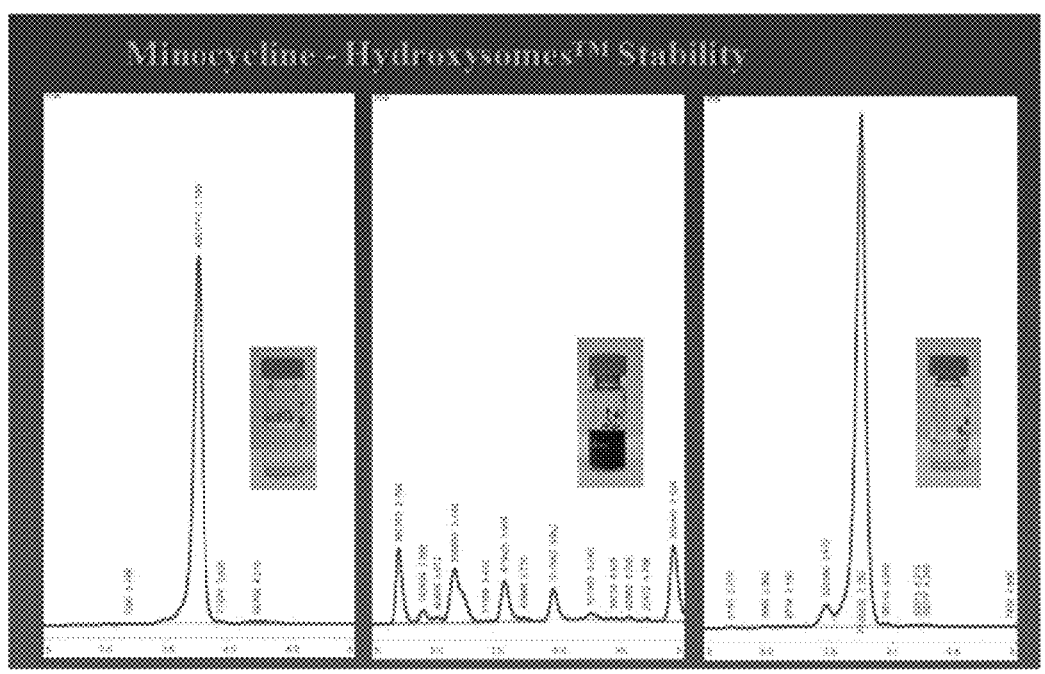
FIG. 1 provides the results of a stability assay reported in the Experimental section below, where the results demonstrate that minocycline associated with porous calcium phosphate particles exhibits greater stability than free minocycline.

Topical minocycline compositions are provided. In some instances, the compositions include an amount of minocycline associated with porous calcium particles, e.g., via entrapment in the pores of the particles and/or ionic binding and/or non-covalent binding to the surface of the particles and/or loosely associated with the particles. Also provided are methods of using the compositions, e.g., in the treatment of acne.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Topical Minocycline Compositions

As summarized above, topical minocycline compositions are provided. The compositions of the invention are formulated for delivery of a minocycline active agent to a topical location of a subject, such as a keratinized skin surface of a mammalian subject, such as a human subject. By keratinized skin surface is meant a skin location of a subject, i.e., a location of the external covering or integument of an animal body. Because the compositions of the invention are formulated for delivery to topical locations, they are formulated so as to be physiologically compatible with the topical location for which they are formulated. Accordingly, when contacted with the target keratinized skin surface for which they are formulated, the formulations do not cause substantial, if any, physiological responses (such as inflammation or irritation) that would render the use of the formulations unsuitable for topical application.

In some instances, the topical minocycline compositions are reduced fluorescence compositions. As such, these compositions exhibit reduced, if any, minocycline generated fluorescence upon excitation with light of an appropriate wavelength, e.g., 365 nm, following topical application. By reduced fluorescence is meant 5-fold or less fluorescence, such as 10-fold or less fluorescence, including 15-fold or less fluorescence, 20-fold or less fluorescence, 25-fold or less fluorescence, 30 fold or less fluorescence, as compared to a control formulation, e.g., water and minocycline hydrochloride. In some instances, the compositions exhibit no fluorescence (e.g., fluorescence is undetectable with naked eye).

As summarized above, compositions of the invention include an amount of a minocycline active agent associated with porous calcium containing particles. As the minocycline active agent is associated with porous calcium particles, it may be entrapped in the pores of the particles and/or ionically bound to the particles and/or non-covalently bound to the particles and/or loosely associated with the particles. As such, the particles may be described as being loaded with an amount of minocycline active agent. By "loaded" is meant that the particles include an amount of minocycline active agent that is associated with the particles. As the minocycline active agent is associated with the particles, the minocycline active agent does not dissociate from the particles in any substantial amount when the particles are present in the delivery composition prior to use. Because substantially none of the minocycline active agent dissociates from the particles, any amount that does dissociate is 40% or less, for example 20% or less, such as 10% or less, including 5% or less of the originally associated amount of minocycline active agent. The amount of minocycline active agent component that is associated with the calcium particles may vary, and in certain embodiments ranges from 0.01 mg/g to 1000 mg/g, such as from 0.1 mg/g to 700 mg/g and including 1 mg/g to 300 mg/g minocycline active agent/gram particles.

As described above, the topical minocycline compositions of interest include an amount of minocycline active agent associated with porous calcium particles, in some instances, the topical compositions include an amount of a UV quencher and/or emission extinguisher and/or both. The topical compositions may further include various delivery vehicles, as well as other components, as desired. These aspects, and others, of the compositions are now reviewed in greater detail.

Porous Calcium Particles

Particles employed in methods of the invention are porous calcium phosphate particles. By "porous" is meant that the particles have a porosity of 30% or more, such as 40% or more, including 50% or more, where the porosity may range from 30% to 200% or more, such as from 40% to 150%, including from 45% to 100%, as determined using a mercury intrusion porosimeter porosity determination protocol as described in ASTM D 4284-88 "Standard Test Method for Determining Pore Volume Distribution of Catalysts by Mercury Intrusion Porosimetry". Porosity is also described by "pore volume (ml/g)" and in such instances many range from 0.01 ml/g to 4.0 ml/g. In some cases, the particles have a porosity such that their internal surface area ranges from 10 $m^2$/g to 150 $m^2$/g, such as from 20 $m^2$/g to 100 $m^2$/g, including 30 $m^2$/g to 80 $m^2$/g, as determined using a BET gas adsorption surface area determination protocol as described in ASTM D3663-03 Standard Test Method for Surface Area of Catalysts and Catalyst Carriers. The pore diameter may vary, ranging in certain instances from 2 to 500 nm, such as 5 to 200 nm, including 10 to 100 nm. In addition, the particles may have a tapping density ranging from 0.2 g/$cm^3$ to 0.5 g/$cm^3$, such as from 0.25 g/$cm^3$ to 0.45 g/$cm^3$, including from 0.3 g/$cm^3$ to 0.4 g/$cm^3$. The tap density can be measured by using standard ASTM WK13023—New Determination of Tap Density of Metallic Powders by a Constant Volume Measuring Method.

In some instances, the particles are rigid particles which are uniform and spherical in shape. By "rigid" is meant that the particles are hard, such that they are not pliant. By "uniform" is meant that the shape of the particles does not vary substantially, such that the particles have substantially the same spherical shape. The term "spherical" is employed in its conventional sense to mean a round body whose surface is at all points substantially equidistant from the center. Of interest in certain embodiments are calcium phosphate particles in which the median diameter is 20 μm or less, such as 10 μm or less, including 5 μm or less, where in some instances the medium diameter is 4 μm or less, such as 3 μm or less, including 2 μm or less.

The particles are, in some instances, chemically pure. By chemically pure is meant that the particles are made up of substantially one type of compound, e.g., a calcium compound, such as a calcium phosphate mineral. Of interest as porous particles are calcium containing particles, such as calcium containing particles that are made of a molecule that includes calcium cation and a suitable anion, e.g., carbonate, phosphate, etc. In some instances, the particles are calcium carbonate particles, such as but not limited to the calcium carbonate particles disclosed in U.S. Pat. Nos. 5,292,495 and 7,754,176. In some instances, the calcium phosphate particles are made up of a calcium phosphate that is described by the molecular formula $Ca_{10}(PO_4)_6(OH)_2$.

In some instances, the particles are ceramic particles. By ceramic is meant that the particles are produced using a method which includes a step of subjecting the particles to high temperature conditions, where such conditions are illustrated below. High temperatures may range from 200 to 1000° C., such as 300 to 900° C. and including 300 to 550° C. In some embodiments, the particles have a compression rupture strength ranging from 20 to 200 MPa, such as from 50 to 150 MPa, and including 75 to 90 MPa, as determined using a SHIMADZU MCT-W500 micro-compression testing machine particle strength determination protocol with a particle sintered at temperature of 400° C. to 900° C., as described in European Patent EP1840661. In some embodiments, the particles are biodegradable, by which is meant that the particles degrade in some manner, e.g., dissolve, over time under physiological conditions. As the particles of these embodiments are biodegradeable under physiological conditions, they at least begin to dissolve at a detectable rate under conditions of pH of 5.8 or less, such as 5.5 or less, e.g., 5.3 or less, including 5 or less, e.g., 4.9 or less.

The porous calcium phosphate particles employed in embodiments of the methods may be prepared using any convenient protocol. In one protocol of interest, the particles are manufactured by spray drying a slurry which includes porous calcium phosphate (e.g., hydroxyapatite) crystals (which may range from 2 nm to 100 nm size range) to produce porous calcium phosphate particles. The resultant particles are then sintered for a period of time sufficient to provide mechanically and chemically stable rigid spheres. In this step, the sintering temperatures may range from 100° C. to 1000° C. for a period of time ranging from 1 hour to 24 hours or more.

Minocycline Active Agent

As summarized above, the compositions of these embodiments include a minocycline active agent. The minocycline active agent may be in the form of a free base, an add salt (e.g., hydrochloride salt) or a mixture thereof. Reference herein to "minocycline" will be understood as encompassing all such forms, unless the context clearly indicates otherwise. An example of a minocycline salt of interest is minocycline hydrochloride (HCl), which has the structure:

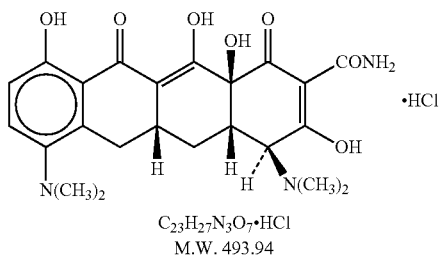

$C_{23}H_{27}N_3O_7 \cdot HCl$
M.W. 493.94

Dosages of minocycline salts will be understood to be on the basis of the amount of minocycline free base provided thereby, and thus may be expressed as a minocycline free base equivalent dosage or amount. Minocycline salts are pharmaceutically acceptable in some embodiments. The term "pharmaceutically acceptable", as used herein, refers to a drug, salt, carrier, etc., that can be introduced safely into an animal body (e.g., taken orally and digested, etc.).

UV Quenchers/Emission Extinguishers

The topical compositions may include an amount of a UV quencher/emission extinguisher. UV quenchers/emission extinguishers of interest include but are not limited to: Allantoin PABA, Benzalphthalide, Benzophenone-1, Benzophenone-2, Benzophenone-3, Benzophenone-4, Benzophenone-5, Benzophenone-8, Benzophenone-7, Benzophenone-8, Benzophenone-9, Benzophenone-10, FD&C Blue No. 1, FD&C Blue No. 2, D&C Blue No. 4, D&C Blue No. 9, FD&C Green No. 3, D&C Green No. 5, D&C Green No, 6, D&C Green No. 8, D&C Orange No. 4, D&C Orange No. 5, D&C Orange No. 10, Benzophenone-11, Benzophenone-12, Benzyl Salicylate, Benzylidene Camphor Sulfonic Add, Bornelone, Bumetrizole, Butyl methoxydibenzoylmethane, Butyl PABA, Cinoxate, DEA-Methoxycinnamate, Dibenzoxazoyl Naphthalene, Diisopropyl Ethyl Cinnamate, Diisopropyl Methyl Cinnamate, Dimorpholinopyridazinone, Drometrizole, Esculin, Ethyl Dihydroxypropyl PABA, Ethyl Diisopropylcinnamate, Ethylhexyl Dimethyl PABA, D&C Orange No. 11, FD&C Red No. 3, FD&C Red No. 4, D&C Red No. 6, D&C Red No. 7, D&C Red No. 17, D&C Red No. 21, D&C Red No. 22, D&C Red No. 27, D&C Red No. 28, D&C Red No, 30, D&C Red No, 31, Ethylhexyl Methoxycinnamate, Ethylhexyl Salicylate, Ethylhexyl Triazone, Ethyl Methoxycinnamate, Ethyl PABA, Ethyl Urocanate, Etocrylene, Glyceryl Ethylhexanoate Dimethoxycinnamate, Glyceryl PABA, Glycol Salicylate, Homosalate, Isoamyl Cinnamate, Isopropylbenzyl Salicylate, Isopropyl Methoxycinnamate, Menthyl Anthranilate, Menthyl Salicylate, Methylbenzylidene Camphor, Octocrylene, Octrizole, PABA, Phenylbenzimidazole Sulfonic Acid, Polyacrylamidomethyl Benzylidene Camphor, D&C Red No. 33, D&C Red No. 34, D&C Red No. 36, D&C Red No. 39, D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No, 11, Potassium Methoxycinnamate, Potassium Phenylbenzimidazole Sulfonate, Red Petrolatum, Sodium Urocanate, TEA-Phenylbenzimidazole Sulfonate, TEA-Salicylate, Terephthalylidene Dicamphor Sulfonic Acid, Titanium Dioxide, Urocanic Acid, Zinc Cerium Oxide.

Coating

Where desired, the minocycline associated calcium particles may include a coating. Coating materials (which may include one or more coating material) of interest are those that may preserve the association of the minocycline active agent with the calcium phosphate particles in various formulations, e.g. formulations designed for topical application to the skin. Suitable coating agents include agents that are physiologically acceptable and are solid at room temperature and are suitable for application to the skin. The coating material component may be a single material or a combination of two or more materials, e.g., where the combination provides for one or more desirable properties.

Materials that find use as coating materials include, but are not limited to waxes, butters, etc., where specific coating materials of interest include: Acrocomia Aculeata Seed Butter, Almond Butter, Aloe Butter, Apricot Kernel Butter, Argan Butter, Attalea Maripa Seed Butter, Avocado Butter, Babassu Butter, Bacuri Butter, Bagura Soft Butter, Baobab Soft Butter, Bassia Butyracea Seed Butter, Bassia Latifolia Seed Butter, Black Currant Seed Butter, Brazil Nut Butter, Camelina Butter, Camellia Butter, Candelilla Butter, Carnauba Butter, Carpotroche Brasiliensis Seed Butter, Chamomile Butter, Cocoa Butter, Coconut Butter, Coffee Butter, Cotton Soft Butter, Cranberry Butter, Cupuacu Butter, Grape Seed Butter, Hazel Nut Butter, Hemp Seed Butter, Horsetail Butter, Wipe Butter, Irvingia Gabonensis Kernel Butter, Jojoba Butter, Karite Butter, Kokum Butter, Kukui Butter, Lavender Butter, Lemon Butter, Lime Butter, Macadamia Butter, Mango Butter, Marula Butter, Mono Butter, Mowrah Butter, Mucaja Butter, Murumuru Butter, Olea Butter, Olive Butter, Orange Butter, Palm Oil, Passion Butter, Phulwara Butter, Pistachio Butter, Pomegranate Butter, Pumpkin Butter, Raspberry Butter, Rice Butter, Sal Butter, Sapucainha Butter, Sesame Butter, Shea Butter, Soy Butter, Tamanu Butter, Sunflower Seed Butter, Sweet almond Butter, Tangerine Butter, Tucuma Seed Butter, Ucuuba Butter, Wheat Germ Butter, acrawax, bayberry wax, beeswax, candelilla wax, castor wax, carnauba wax, ceresin wax, esparto wax, glycowax, jojoba wax, Japan wax, lignite wax, linear polyethylene wax, microcrystalline petroleum wax, montan wax, ouricouri wax, ozokerite wax, paraffin wax, rice bran wax, shellac wax, silicone waxes, synthetic waxes, sugarcane wax, petrolatum, hard tallow, cetyl alcohol, lanolin alcohol, lanolin, stearyl alcohol, stearone, glyceryl monostearate, glyceryl distearate, glycerol palmitostearate, cetyl palmitate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene homopolymers, ethylene-propylene copolymers, ethylene-hexene copolymers, ethylene glycol methacrylate, and/or polyethylene glycols, such as PEG 18, PEG-20, PEG 32, PEG-75, PEG-90, PEG-100, and PEG-180.

Delivery Component

The topical compositions of the invention may include an amount of the minocycline active associated calcium particles combined with a delivery composition component. The delivery composition component refers to that portion of the non-fluorescent topical composition that is not the minocycline active agent bound particles. The amount of minocycline active agent associated particles that is present in the delivery composition and therefore combined with a delivery composition component may vary. In some embodiments, the amount of minocycline active agent associated with particles that is present in the delivery composition and therefore combined with other delivery composition components may vary. In some embodiments the amount of minocycline active agent associated with particles ranges from 0.01 to 200 mg/g, such as 0.1 to 100 mg/g and including 1 to 50 mg/g active agent bound particles per gram of delivery composition component.

Delivery vehicles of interest include, but are not limited to, compositions that are suitable for applications via one or more of oral, topical, implantation, ocular, aural, rectal, vaginal, etc., routes. In certain embodiments, the vehicle is formulated for application to a topical region or surface of a subject, such as a keratinized skin surface. The subject compositions may be formulated as stable solutions or suspensions of the components, e.g., in an aqueous solvent. Where desired, the components may be combined with one or more carrier materials to form a solution, suspension, gel, lotion, serums, cream, ointment, aerosol spray, roll-on, foam products, mousses, powders, sticks, or the like, as desired. Of interest in certain embodiments are aqueous delivery vehicles, i.e. aqueous vehicles that include a certain amount of water.

The topical composition may also contain other physiologically acceptable excipients or other minor additives, particularly associated with organoleptic properties, such as fragrances, dyes, buffers, cooling agents (e.g. menthol), coating materials or the like.

Lotions (as well as other topical formulations) of interest may include one or more of the following components: Water, Viscosity modifiers, Humectants, Vegetable oils and hydrogenated vegetable oils, Emollients, Silicone, Conditioning Agents, Emulsifiers, Glyceryl Esters of Fatty Adds, Silicone, C1-C30 monoesters and polyesters of sugar, Conditioning Agents, Preservatives, etc. Depending on the topical formulation, additional components of interest include: Abrasives, Absorbents, Antimicrobial and antifungal agents, Astringents, Anti-Acne agents, Anti-wrinkle agents, Antioxidants, Antimicrobials, Binders, Biological actives, Suffering actives, Bulking actives, Chelating agents, Chemical additives, External analgesics, Film former agents, Opacifying agents, pH adjusters, Reducing agents, Colorants, Fragrances, Cosmetic Soothing Agents, Tanning actives & accelerators, Skin lightening/whitening agents, Sunscreens, Surfactants, Skin Conditioning Agents, Vitamins, etc.

As indicated above, of interest in certain embodiments are semi-solid delivery compositions, such as gels, creams and ointments. Such compositions may be mixtures of (in addition to the active agent) water, water soluble polymers, preservatives, alcohols, polyvalent alcohols, emulsifying agents, wax, solvents, thickeners, plasticizers, pH regulators, water-retaining agents and the like. Furthermore, such compositions may also contain other physiologically acceptable excipients or other minor additives, such as fragrances, dyes, buffers, coating materials or the like.

Methods of Making Delivery Compositions

Aspects of the invention further include methods of making the topical compositions. While any convenient fabrication protocol may be employed, in some instances the methods of fabrication include combining an amount of a minocycline active agent associated particles with a delivery composition component to produce the desired delivery composition. The active agent associated particles may be produced using any convenient protocol. One protocol of interest includes combining a liquid composition of the active agent, such as an aqueous composition of the active agent, with a liquid composition of the porous calcium particles (with agitation where desired) under conditions sufficient to produce the desired active agent bound particles. Following production of the desired active agent associated particles, the resultant particles are then combined with the delivery composition component using any convenient protocol. The particular protocol employed may vary depending on the nature of the delivery composition component, where in certain instances the delivery composition component and active agent loaded particles may be combined with mixing to produce the desired delivery composition.

Methods of Use

In practicing methods of the invention, a topical minocycline composition is applied to a topical region of a subject and maintained at the topical region for a period of time sufficient to result in the desired delivery of the minocycline active agent to the subject, as described above. The topical region is, in certain embodiments, a keratinized skin region. The keratinized skin region, including haft follicles, sweat glands and sebaceous glands, may be present at a variety of locations, e.g., limbs, arms, legs; torso, e.g., chest, back, stomach; head, e.g., neck, face; etc. In certain embodiments, the region will be a head region, such as a facial region, e.g., forehead, occipital region, around the mouth, on the nose, etc. The topical region to which the composition is applied may vary with respect to area, ranging in certain embodiments from 1 $mm^2$ to 300 $cm^2$ or more such as from 1 to 50 $cm^2$, and including from 3 to 10 $cm^2$.

Following application, the composition is maintained at the site of application for a period of time sufficient for a desired therapeutic outcome to occur, e.g., amelioration of a symptom(s) of interest, reducing acne. The period of time may vary, and in certain embodiments ranges from 1 min to 24 hours or longer, such as from 30 min to 12 hours and including from 1 hour to 12 hours.

In practicing the subject methods, a subject may be administered a single dose or two or more doses over a given period of time. For example, over a given treatment period of one month, 1 or more doses, such as 2 or more doses, 3 or more doses, 4 or more doses, 5 or more doses, etc., may be administered to the subject, where the doses may be administered weekly or daily or even multiple times per day.

Methods of the invention may result in decreased fluorescence of the minocycline active agent when the active agent is associated with porous calcium particles as compared to a suitable control, such as a composition made up of the minocycline active agent and water, where the minocycline active agent is not bound to porous calcium particles. The observed decrease in fluorescence as compared to a control may have a magnitude of a factor of 2-fold or more, such as 5-fold or more, including 10-fold or more, including 25-fold or more, 50-fold or more or 75 fold or more.

Methods of the invention may include a step of diagnosing a subject as being a subject in need of topical minocycline administration. For example, the methods may include assessing whether a subject is suffering or likely to suffer from acne and determining that topical minocycline administration is desirable in order to treat the acne and/or prevent occurrence of the acne.

The subject methods and compositions may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects or patients are humans.

Utility

The compositions and methods of the invention find use in a variety of different applications in which it is desired to topically deliver a minocycline active agent to a subject. In delivering minocycline active agents to a topical location of a subject, formulations of the invention may deliver the minocycline active agent bound particles at least into an epidermal location that is beneath the skin surface of a subject. As such, embodiments of the invention include methods of delivering minocycline active agent loaded particles into the stratum corneum of a subject, where the methods may result in delivery of the minocycline into the deep stratum corneum and/or dermis of a subject, By "deep stratum corneum" is meant a region that is 2 or more cell layers below the skin surface, such as 5 or more cell layers below the skin surface, including 10 or more cell layers below the skin surface. In some instances, the minocycline is delivered to region of the stratum corneum that is 2 μm or more, such as 5 μm or more and including 15 μm or more below the surface of the skin. In some instances, the minocycline is delivered to regions below the stratum corneum into the epidermis, such that it is delivered to 50 μm or more below the stratum corneum, such as 100 μm or more below the stratum corneum and including 180 μm or more below the stratum corneum. In some instances, the minocycline is delivered to regions below the epidermis into the dermis region, such that it is delivered 500 μm or more below the epidermis, such as 1000 μm or more below the epidermis and including 1400 μm or more below the epidermis.

Upon contact with the topical location, the minocycline active agent bound particles begin to release their minocycline active agent "payload" and break down (e.g., via dissolution caused by pH gradient of the skin), as the porous particles dissociate under acidic conditions, e.g., conditions of pH 6 or lower, such as 5.5 or lower, including 4.90 or lower, such as the physiological acidic conditions of the stratum corneum. The time required for partial dissolution of particles in the stratum corneum may vary, and in certain embodiments ranges from 1 minute to 24 hours, such as 10 minutes to 12 hours and including 30 minutes to 3 hours, over which time period active agent is released from the active agent bound particles. The proportion of active agent that is released from the active agent bound particles may vary, and in certain instances is 1% or more, such as 10% or more, including 50% or more (w/w). When the particles are delivered to skin, the minocycline active agent component associated with the particle can dissociate from the particle in amounts ranging from 0.1. to 100%, in some instances delivering into the skin 50% or less, 40% or less, 30% or less, 20% or less, 10% or less, 5% or less, including 2% or less of the minocycline active agent associated with the particles.

In some embodiments, the compositions and methods are used to treat acne, Acnes of interest include, but are not limited to: acne vulgaris; acne rosacea; acne conglobata; acne fulminans; gram-negative folliculitis; pyoderma faciale; and combinations thereof. The acne may be a severe form of acne, a moderate form of acne, or a mild form of acne, and may include inflammatory and/or non-inflammatory lesions. In some embodiments, the compositions and methods described herein can be used to treat inflammatory lesions of acne vulgaris.

Effective treatment of acne may be characterized in various ways. For example, effective treatment of acne may be characterized as a reduction, and in some embodiments a substantial reduction, in the number of acne lesions. The acne lesions may be defined as at least one of inflammatory and non-inflammatory lesions. Effective treatment of acne may be characterized as a reduction in the severity of acne. Effective treatment of acne may be characterized as a reduction in the duration of an outbreak. For example, a composition described herein may reduce the duration that a lesion will remain after it has formed. Effective treatment of acne may be characterized as a reduced probability of an acne-related symptom. For example, a composition described herein may reduce the probability of developing further lesions.

In some embodiments, the acne is at least partially caused by hormonal changes, excessive production of one or more male hormones, or pregnancy. The acne may be caused by a medication, such as a contraceptive pill, ointments for eczema, or medicine for epilepsy. The acne may be caused by a drug, such as androgens, lithium, or barbiturates.

The following examples are offered by way of illustration and not by way of limitation.

EXPERIMENTAL

1. Materials and Methods

A. Materials

1. Hydroxysomes® (INCl Name: Hydroxyapatite, Laboratory Skin Care, Inc. Lot No. 0712-2701) was used for the binding, releasing and fluorescence study.
2. Minocycline Hydrochloride (HCl), 4,7-Bis(dimethylamino) 1,4,4a,5,5a,6,11,12a-octahydro-3,10,12,12a-tetrahydroxy-1,11-dioxo-2-naphthacenecarboxamide monohydrochloride, Manufacturer: Sigma-Aldrich Product No.: M 9511 (Lot No. 078K1053), CAS No.: 13614-98-7

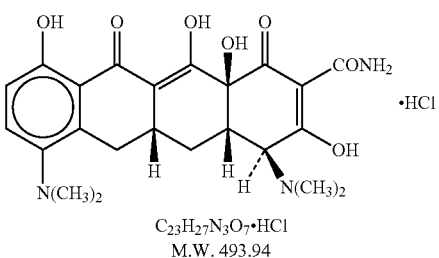

C₂₃H₂₇N₃O₇·HCl
M.W. 493.94

Structure of Minocycline HCl 3. 1% w/v minocycline/water, Batch # RNB7132, kept at 4° C. in dark.

B. Minocycline HCl Detection by UV-Vis Spectroscopy

The spectra of minocycline solution in water were obtained with Shimadzu spectrophotometer (Model number UV-1650PC, Detection at UV 273 nm,)

C. Binding of Minocycline HCl to Hydroxysomes®

Hydroxysomes® (calcium phosphate particles, Laboratory Skin Care, San Carlos, Calif.) were suspended in water. Minocycline solution (0.01-20 mg/ml in water) was added. The final pH of the suspension was adjusted to 6.2 to 8.0 with add. The binding suspension was mixed by shaking for 30 min.

The binding suspensions were centrifuged at 10,000 rpm for 10 min in the bench top microcentrifuge. The supernatants were analyzed with the Shimadzu spectrophotometer to quantify the free minocycline.

The bound minocycline was calculated by subtracting the amount of the minocycline detected in the supernatant, from the total initial amount in the binding suspension. The total initial minocycline absorbance at the binding pH was calculated from the linearity equation of the standard plot.

Controls: Minocycline solution at the same pH with the same concentration as in the binding mixture.

D. Example Formulation

| Nr. | Raw Material | INCI Name | % w/w |
|---|---|---|---|
| 1 | Purified Water | Purified Water | 88.67 |
| 2 | Xanthan Gum | Xanthan Gum | 0.30 |
| 3 | Glycerin | Glycerin | 0.99 |
| 4 | CCT | Caprylic/Capric Triglyceride | 2.98 |
| 5 | Stearyl Alcohol | Stearyl Alcohol | 1.99 |
| 6 | Cetyl Alcohol | Cetyl Alcohol | 1.99 |
| 7 | Ritapro 165 | Glyceryl Stearate, PEG-100 Stearate | 0.99 |
| 8 | Euxyl PE 9010 | Phenoxyethanol, Ethylhexylglycerin | 0.99 |
| 9 | Sepiplus 400 | Polyacrylate-13, Polyisobutene, Polysorbate 20 | 0.50 |
| 10 | Minocycline HCl-Hydroxysomes™ | Minocycline HCl, Hydroxyapatite | 0.60 |
|  | TOTAL: |  | 100.0% |

II. Results

A. Minocycline Binding and Release from Hydroxysomes®

Minocycline attaches to Hydroxysomes™ at pH of 6.2-8.0. Minocycline associated with Hydroxysomes™ is unstable at lower than pH 5, for example pH 4.7 or less. Therefore, minocycline releases from Hydroxysomes™ (upon delivery into the skin.

B. Fluorescence Assessment of the Formulation

A Minocycline-HCl 0.1% (wt/wt) solution was prepared with 0.1 mL of water and 0.05 g of Hydroxysomes®. This was added to the formulation above. The formulation was then applied on the filter paper to assess the fluorescence emission. The fluorescence emission was assessed visually with using a commercial black light (MR. LIGHT T5 14 W, UV peak wave length around 365 nm) as an excitation source. The fluorescence emission was not observed with the control sample without Hydroxysomes®. The minocycline-HCl sample in the cream without Hydroxysomes® emitted yellow-green fluorescence with the excitation of the black light. The minocycline-HCl sample containing Hydroxysomes® emitted no fluorescence.

III. Conclusions

The above results demonstrate the development of the following:

1. Hydroxysomes® bind Minocycline HCl at neutral or alkaline pH and release minocycline at acidic pH;
2. Minocycline HCl-Hydroxysomes® substantially reduced the fluorescence in the topical formulation.

VI. Additional Characterization of Minocycline-Hydroxysomes® Complexes

A. Minocycline Stability

Minocycline-Hydroxysomes® (25 mg/g) and minocycline alone (2.5 mg/mL) were added to water in glass vials and the vials capped and stored at room temperature for 6 days. The vials were then centrifuged and the supernatant analyzed by HPLC. The vial containing minocycline became visibly discolored during the test, and HPLC analysis revealed substantial degradation of minocycline with the occurrence of several unidentified peaks were observed. In contrast, no discoloration was observed in the minocycline Hydroxysomes® vial and no additional peaks other than minocycline were observed with HPLC analysis. See FIG. 1.

C. Minocycline Release at Skin pH

Figure 2:
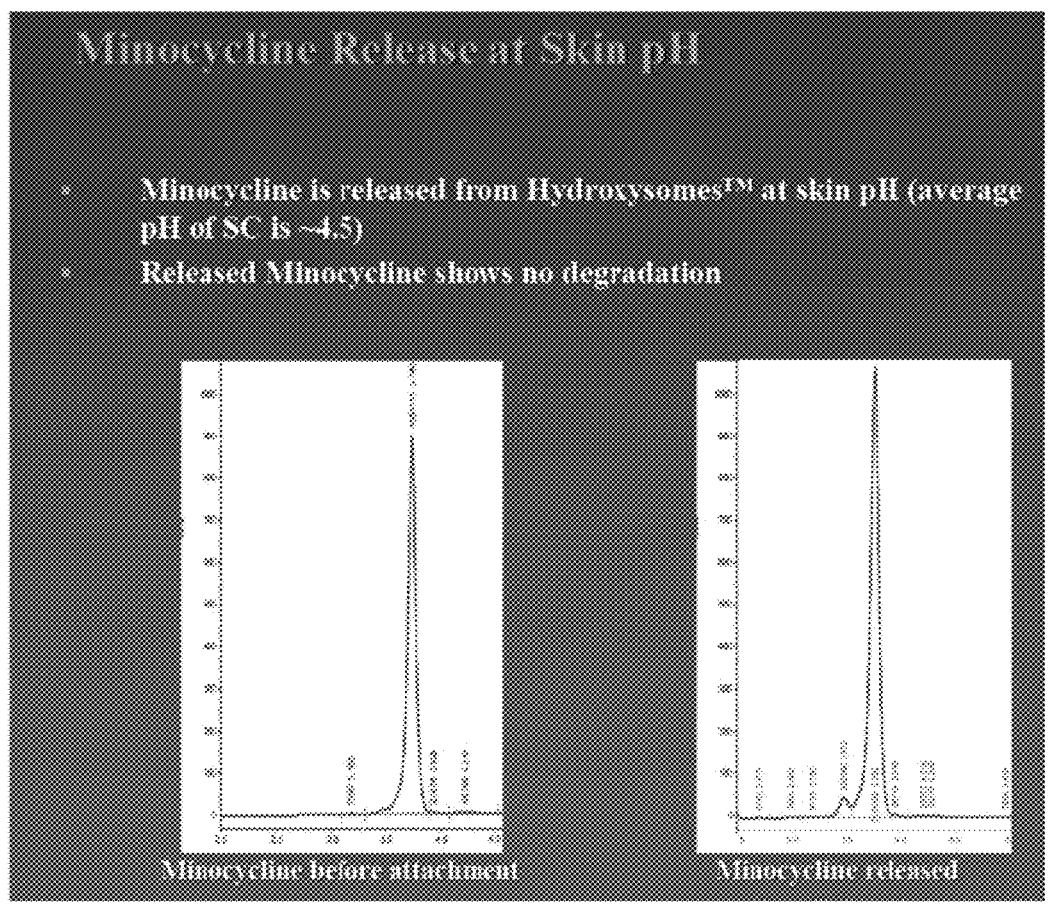
FIG. 2 provides the results of a pH release assay reported in the Experimental section below, where the results demonstrate that minocycline associated with porous calcium particles is released at stratum corneum skin pH conditions and is not degraded when released.

Minocycline-Hydroxysomes® (25 mg/g) were added to 0.5 M sodium acetate buffer at pH 4.5. This buffer was used to represent the average pH of stratum corneum. The suspension was nixed for 1 hour, centrifuged and the supernatant analyzed for minocycline by HPLC. 92% of minocycline was released under these conditions. The HPLC retention time of the released MNC was no different from the minocycline standard, indicating that minocycline remained chemically unchanged during and after bound to Hydroxysomes®. See FIG. 2

D. Minocycline Fluorescence

Figure 3:
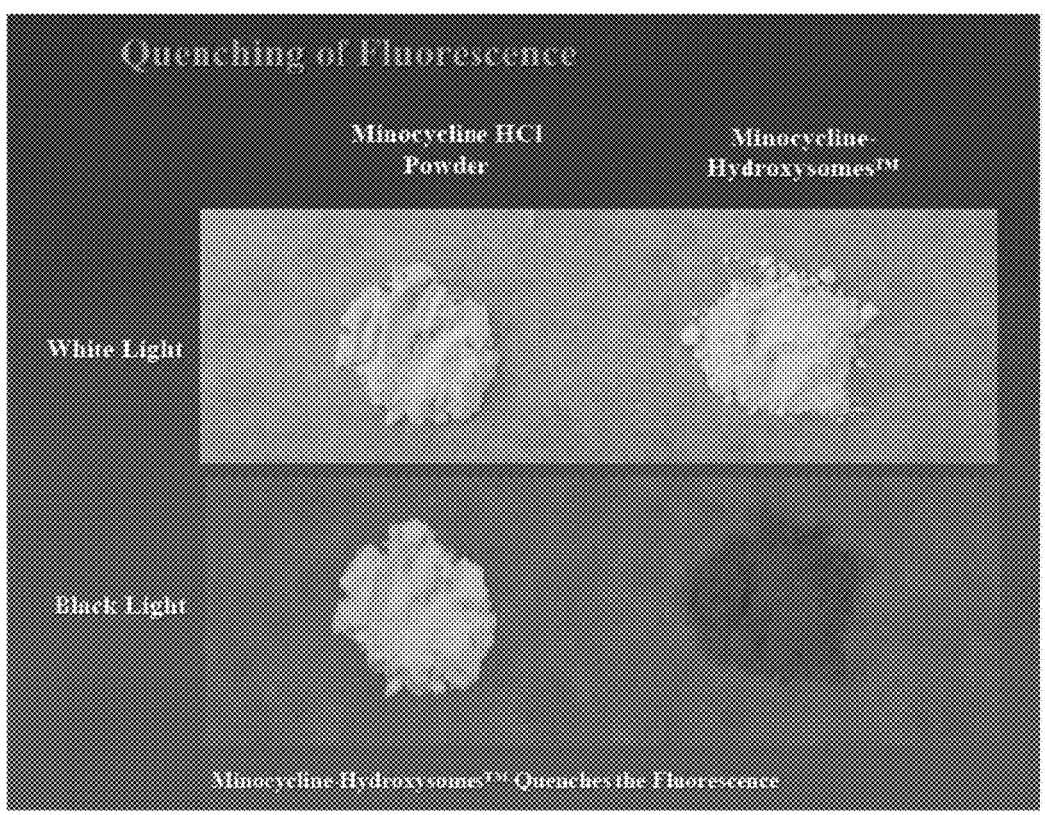
FIG. 3 provides a picture of both free minocycline powder under white light and black light. The picture shows that minocycline associated with porous calcium phosphate particles exhibits less fluorescence than free minocycline.

Minocycline-HCl and minocycline-Hydroxysomes® were imaged under white light and UV black light to detect fluorescence. Bulk powders of minocycline and minocycline-Hydroxysomes® (25 mg MNC/g Hydroxysomes™) were placed under white and black light and photographs taken with a digital camera. Intense yellow-orange fluorescence was observed with minocycline powder, but no fluorescence was observed with MNC-Hydroxysomes®. See FIG. 3.

Figure 4:
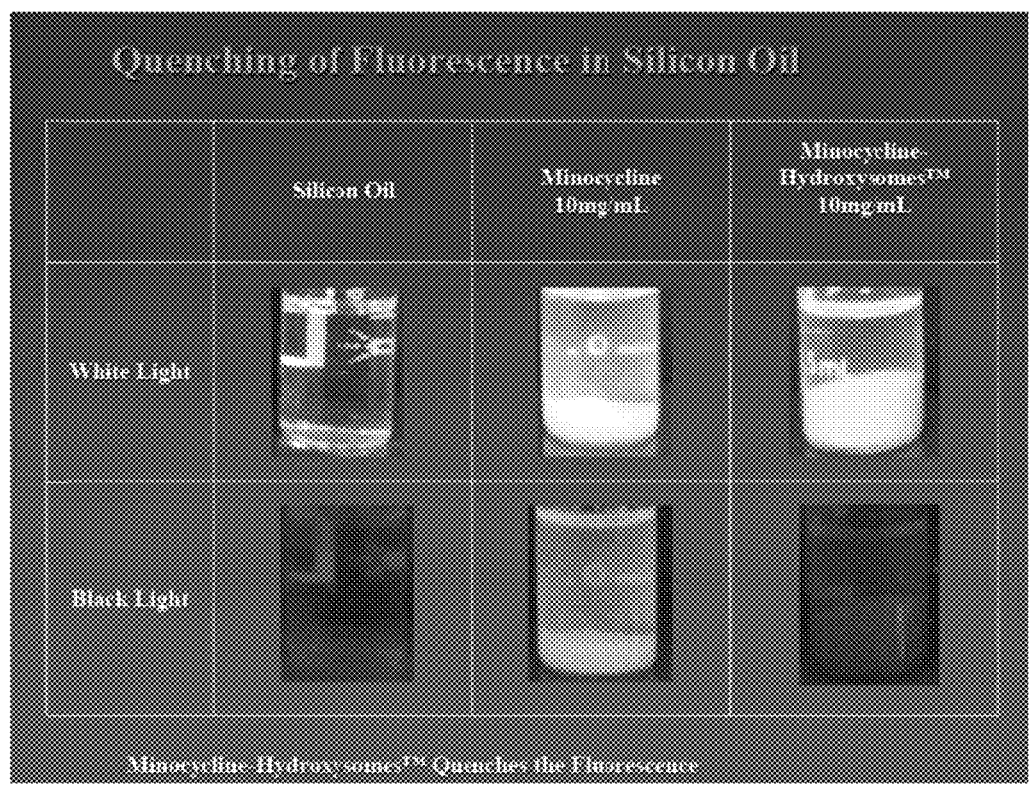
FIG. 4 provides a picture of silicone oil, silicone oil containing free minocycline, and silicone oil containing minocycline associated with porous calcium phosphate particles. The picture shows that minocycline associated with porous calcium phosphate particles exhibits less fluorescence than free minocycline.

Minocycline and minocycline-Hydroxysomes® were then dispersed in silicone oil at 2% minocycline (w/v) and imaged by digital camera. Minocycline is not soluble in silicone oil so the fluorescence of the solid material can be observed. Under white light, the yellow color of minocycline was similar to that of minocycline-Hydroxysomes®. Under black light, however, the strong yellow-orange fluorescence was still observed from minocycline, while low, diffuse fluorescence was observed from minocycline-Hydroxysomes®. The silicone oil control exhibited no fluorescence. Close-up images of the oil revealed intense fluorescence from the settled minocycline, in contrast to diffuse fluorescence on the minocycline-Hydroxysomes® surface. See FIG. 4.

E. Dermal Delivery of Minocycline in Human Skin

The dermal delivery of minocycline was determined at 2, 4 and 12 hours. For the 2-hour measurement, minocycline-Hydroxysomes® was applied to the skin surface in a static penetration cell. For the 4- and 12-hour measurements, minocycline-Hydroxysomes® was applied to the skin in flow-through diffusion (Franz) cells. Fresh human tissue was obtained from surgery, maintained with growth supplements and antibiotics prior to the experiments and used within 7 days of receipt. To determine skin penetration of minocycline, the skin surface was rinsed and the skin separated into epidermis and dermis using the heat separation method. The epidermis and dermis were then extracted in 80% methanol and the extract analyzed for minocycline by HPLC.

Figure 5:
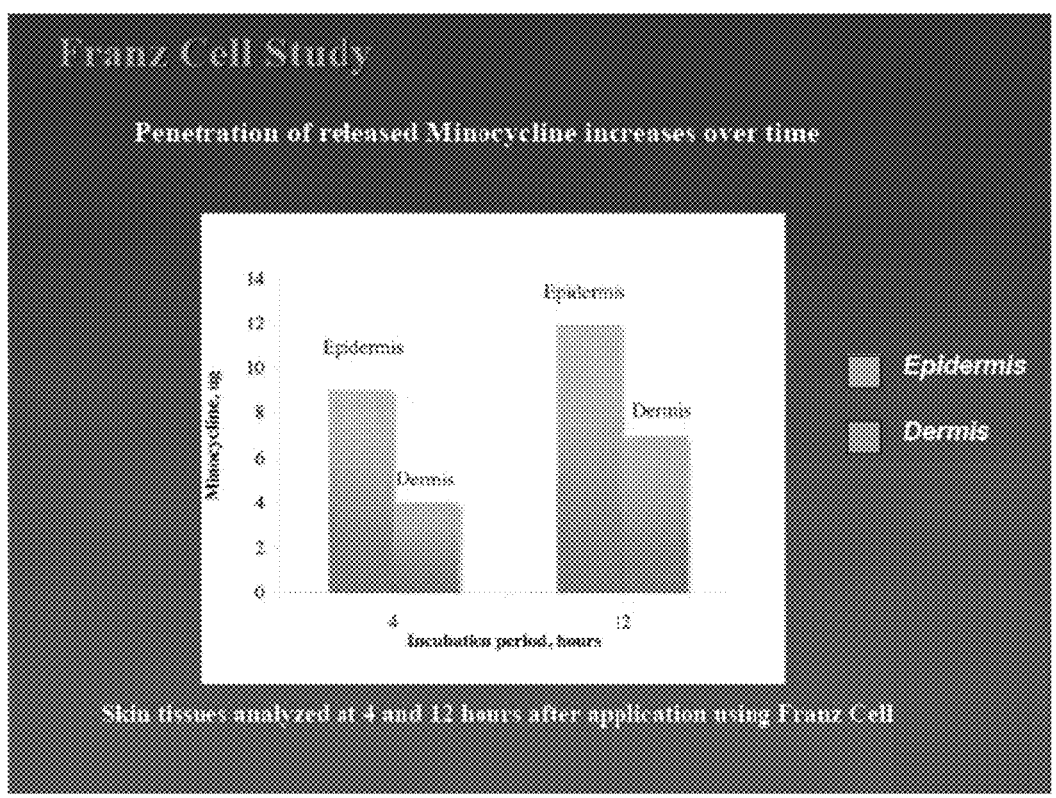
FIG. 5 graphically provides the results of a dermal delivery assay reported in the Experimental section, below. The results show that minocycline associated with porous calcium phosphate particles is delivered in a sustained release manner into the skin.

The penetration of minocycline into skin from minocycline-Hydroxysomes® increased over time. By separating the skin into epidermis and dermis, the depth of penetration was determined by analyzing minocycline concentration in the separated tissue layers. Levels of minocycline were higher in the epidermis and dermis at 12-hours compared to 4 hours. These results show that minocycline when delivered bound to Hydroxysomes® penetrated into the deeper layers of the skin. Two (2)% of the applied minocycline was absorbed in skin after 12 hours. See FIG. 5.

Although the foregoing invention has been described in some detail by way of Illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A topical minocycline composition comprising porous ceramic calcium particles loaded with a minocycline active agent, wherein the composition is a formulation configured to be applied to a keratinized skin surface location of a mammal and exhibits reduced fluorescence as compared to a control.

2. The topical minocycline composition according to claim 1, wherein the porous calcium particles are porous calcium phosphate particles.

3. The topical minocycline composition according to claim 1, wherein the particles have a pore volume ranging from 30 to 85%.

4. The topical minocycline composition according to claim 3, wherein the particles have a pore size ranging from 2 nm to 100 nm.

5. The topical minocycline composition according to claim 4, wherein the particles are produced by:
    preparing a fluid composition of calcium phosphate crystals;
    drying the fluid composition in a manner sufficient to produce precursor particles; and
    subjecting the precursor particles to elevated temperatures in a manner sufficient to produce uniform, rigid, spherical nanoporous calcium phosphate particles.

6. The topical minocycline composition according to claim 1, wherein the formulation is a cream.

7. The topical minocycline composition according to claim 1, wherein the minocycline is bound to the particles in an amount ranging from 0.01 to 2000 mg minocycline per gram of particles.

8. The topical minocycline composition according to claim 1, wherein the particles have an average particle diameter of 2 microns or less.

9. The topical minocycline composition according to claim 1, wherein the minocycline active agent comprises a minocycline salt.

10. A method comprising applying to a keratinized skin surface location of a subject a topical minocycline composition comprising porous ceramic calcium particles loaded with a minocycline active agent, wherein the composition is a formulation configured to be applied to a keratinized skin surface location of a mammal and exhibits reduced fluorescence as compared to a control.

11. The method according to claim 10, wherein the particles are calcium phosphate particles.

12. The method according to claim 10, wherein the particles have a pore volume ranging from 30 to 85%.

13. The method according to claim 12, wherein the particles have a pore size ranging from 2 nm to 100 nm.

14. The method according to claim 10, wherein the amount of minocycline active agent associated with the particles ranges from 0.01 to 2000 mg minocycline per gram of particles.

15. The method according to claim 10, wherein the particles have an average particle diameter of 2 microns or less.

16. The method according to claim 10, wherein the method is a method of treating acne.

17. The composition according to claim 1, wherein the particles are described by the molecular formula $Ca_{10}(PO_4)_6(OH)_2$.

18. The composition according to claim 2, wherein the calcium phosphate particles are chemically pure.

19. The method according to claim 10, wherein the particles are described by the molecular formula $Ca_{10}(PO_4)_6(OH)_2$.

20. The method according to claim 11, wherein the calcium phosphate particles are chemically pure.

* * * * *

UNITED STATES PATENT AND TRADEMARK OFFICE
CERTIFICATE OF CORRECTION

PATENT NO. : 10,080,764 B2  
APPLICATION NO. : 15/380829  
DATED : September 25, 2018  
INVENTOR(S) : Zahra Mansouri Page 1 of 1

It is certified that error appears in the above-identified patent and that said Letters Patent is hereby corrected as shown below:

In the Specification

Please replace "Add" with -- "Acid" -- (Column 6, Line 9).

Please replace "Wipe" with -- "Illipe" -- (Column 6, Line 64).

Please replace "Mono" with -- "Monoi" -- (Column 6, Line 67).

Please replace "Adds" with -- "Acids" -- (Column 8, Line 1).

Please replace "Suffering" with -- "Buffering" -- (Column 8, Line 7-8).

Please replace "haft" with -- "hair" -- (Column 8, Line 54).

Please replace "add" with -- "acid" -- (Column 11, Line 27).

Please replace "nixed" with -- "mixed" -- (Column 12, Line 40).

Signed and Sealed this  
Twenty-seventh Day of November, 2018

Andrei Iancu  
*Director of the United States Patent and Trademark Office*